United States Patent [19]

Anapliotis

[11] Patent Number: 5,061,246
[45] Date of Patent: Oct. 29, 1991

[54] TUBE-LIKE COVERING FOR PROTECTING A SURGICAL INSTRUMENT, AND METHOD OF MAKING

[75] Inventor: Emmanuel Anapliotis, Berlin, Fed. Rep. of Germany

[73] Assignee: Effner GmbH, Berlin, Fed. Rep. of Germany

[21] Appl. No.: 443,944

[22] Filed: Dec. 1, 1989

[30] Foreign Application Priority Data

Dec. 1, 1988 [DE] Fed. Rep. of Germany 8815076[U]
Apr. 20, 1989 [DE] Fed. Rep. of Germany 8905102[U]

[51] Int. Cl.$^5$ ............................................... A61M 5/00
[52] U.S. Cl. ............................ 604/171; 604/172; 604/192; 604/263; 206/210
[58] Field of Search .............. 604/110, 171, 172, 198, 604/263, 187, 192, 197; 206/210, 305, 363, 364, 365

[56] References Cited

U.S. PATENT DOCUMENTS

| | | | |
|---|---|---|---|
| 3,796,477 | 3/1974 | Geraci . | |
| 3,809,072 | 5/1974 | Ersek et al. . | |
| 3,967,728 | 7/1976 | Gordon et al. | 206/364 |
| 4,725,267 | 2/1988 | Vaillancourt | 604/263 |
| 4,754,877 | 7/1988 | Johansson et al. | 206/364 |
| 4,897,083 | 1/1990 | Martell | 604/198 |
| 4,935,011 | 6/1990 | Hogan | 604/263 |

FOREIGN PATENT DOCUMENTS

| | | |
|---|---|---|
| 0201257 | 11/1986 | European Pat. Off. . |
| 0298685 | 1/1989 | European Pat. Off. . |
| 406507 | 11/1924 | Fed. Rep. of Germany . |
| 808362 | 7/1951 | Fed. Rep. of Germany . |
| 2527695 | 12/1976 | Fed. Rep. of Germany . |
| 8815549 | 2/1989 | Fed. Rep. of Germany . |
| 1099920 | 1/1968 | United Kingdom . |
| 81/03609 | 12/1981 | World Int. Prop. O. . |

OTHER PUBLICATIONS

European Search Report, EF 38.16-EU, Apr. 3, 1990, three pages.

Primary Examiner—Richard J. Apley
Assistant Examiner—Lynne Reichard
Attorney, Agent, or Firm—Spencer & Frank

[57] ABSTRACT

A thin covering is used for protecting an elongated surgical instrument, and is initially in a telescopically folded configuration prior to insertion of the surgical instrument therein, comprising: an elongated tube having an insertion opening region; two resiliently deformable leaf-shaped lining members connected to the elongated tube disposed in the insertion region, the lining members each having a central portion and a pair of sides edges. A first of the pair of side edges of one of the lining members is substantially congruent to a first of the pair of side edges of the other of the lining members, and a second of the pair of side edges of the one of the lining members is substantially congruent to a second of the pair of sides edges of the other of the lining members. Upon application of forces urging each of the first and the second pair of side edges together, the central portions are spread apart to form a jaw for receiving the surgical instrument.

12 Claims, 5 Drawing Sheets

TUBE-LIKE COVERING FOR PROTECTING A SURGICAL INSTRUMENT, AND METHOD OF MAKING

CROSS-REFERENCE TO RELATED APPLICATION

The present disclosure relates to the subject matter disclosed in German Application Nos. G 88 15 076.3 and G 89 05 102.5 of Dec. 1, 1988 and Apr. 20, 1989, respectively, the entire specifications of which are incorporated herein by reference.

BACKGROUND OF THE INVENTION

The present invention relates to a thin covering folded in a telescopic manner as protection for a rod-like surgical instrument.

Thin coverings are known which serve to protect surgical instruments against septic contamination during surgery. In particular, highly sensitive surgical optical instruments, such as, for example, endoscopes, arthroscopes, orthoscopes, or surgical lasers require protective sheathings since it is difficult to sterilize them and accordingly they should not be contaminated. Use of a sheathing in the form of a sterile tube-like covering, however, eliminates the need for sterilization of the covered portions. Such thin coverings are intended for one-time use only.

Due to the great number of possible applications, different thin coverings have become known whose shapes vary according to their intended use. Thin coverings are known having a distinctly tubular shape with tube widths in a range from centimeters to decimeters and tube lengths in a range from decimeters to meters. For thin coverings having long lengths, the application of particularly tight coverings and the introduction into a thin covering of a surgical instrument, are often difficult tasks which require considerable skill.

SUMMARY OF THE INVENTION

It is an object of the present invention to facilitate o handling of a thin covering of the above-mentioned type, and in particular to facilitate pulling the thin covering over a surgical instrument and to facilitate introduction of the surgical instrument into the thin covering.

It is another object of the invention to provide a simple method for telescoping a thin covering according to the invention into a configuration suitable for introduction of a surgical instrument.

The above and other objects are accomplished according to one aspect of the invention in that a thin covering is provided for protecting an elongated surgical instrument, the thin covering being initially in a telescopically folded configuration prior to insertion of the surgical instrument therein, and comprises:

an elongated tube having an insertion opening region;

two resiliently deformable leaf-shaped lining members connected to the elongated tube disposed in the insertion region, the lining members each having a central portion and a pair of side edges a first of the pair of side edges of one of the lining members being substantially congruent to a first of the pair of side edges of the other of the lining members, and a second of the pair of side edges of the one of the lining members being substantially congruent to a second of the pair of side edges of the other of the lining members, and wherein upon application of force urging each of the first and the second pair of side edges together, the central portions are spread apart to form a jaw for receiving the surgical instrument.

According to the invention, uncomplicated opening and closing of a flexible tube-like covering which includes a thin tube having a manually openable closed end can be realized by provision of two leaf-shaped flexible lining members or strips in a opening region of the tube-like covering which, when in a rest position, lie flat against one another. Slight pressure with the fingers or thumbs on respective opposite edge regions of the lining members causes the lining members to deform resiliently apart except at their opposite edge regions, so that they form a jaw-like opening. It is thereby possible, even during a surgical operation, for an operator to easily and quickly open the tube-like covering with only one hand, the opening in the tube-like covering being large enough and stable enough for the secure introduction of the instrument.

By providing the opening region of the thin covering of the flexible tube-like covering mentioned above with the two leaf-shaped flexible lining members in the form of flexible strips whose double length corresponds to the circumference of the opening region and whose width is at least a few centimeters, the insertion process for inserting an instrument into the flexible tube-like covering is simplified and accelerated. Further, due to telescopic folding of the covering prior to introduction of the instrument, any searching by the operator for a "correct" insertion opening in the flexible tube-like covering is eliminated since pressure on the sides of the two leaf-shaped flexible lining members will always spread open the opening region of the tube-like covering instead of a lateral fold thereof.

The two flexible lining members or strips are preferably composed of materials such as cardboard strips, thin plastic sheets, or metal foils. The thickness of the material forming these two flexible strips is preferably selected in such a way that, on the one hand, it is possible to manually resiliently deform the two flexible strips from an initial configuration in which the flexible strips are in contiguous contact with each other to a second configuration in which the two flexible strips form a jaw-like opening and to thereafter maintain the jaw-like opening of the two flexible strips for a relatively long period of the time with relatively little effort and, on the other hand, the resilient flexibility of the material is substantially retained such that, upon removal of the manual pressure on the two lining members at the end of the insertion process, the two lining members resiliently snap back into their initial, unbiased positions.

According to an advantageous modification of the invention, the spreading operation is facilitated by the provision of two lining members which each are in the form of curved sections, with such preferential curvatures being a product both of the manufacturing process employed as well as the material involved, the two lining members being oriented so that their convex sides face outwardly from each other. The two lining members each have an axial direction which extends in the longitudinal direction of the thin covering when in the initial configuration Each of the two lining members preferably has a rectangular shape and correspond to the width of an adjacent portion of the thin, flexible covering tube in the flattened initial configuration. The two lining members continue as an extension of the thin, flexible tube in the longitudinal direction. In particular, the two lining members project in the form of a tab beyond the edge of the adjacent region of the thin, flexible tube. The two lining members can additionally be provided with gripping holes for further facilitating the pulling apart of the telescoped folds of the tube-like covering when in a folded configuration. The two lining members may be glued or welded to an interior surface of the adjacent region of the thin, flexible tube used in the tube-like covering In operation, the two lining members of the tube-like covering—still in its telescoped configuration—are caused to be spread apart into a jaw-like opening, an instrument is pushed into the telescoped tube-like covering, and a distal end of the instrument is fixed to a respective distal end of the tube-like covering by way of fastening means provided there. By pushing the instrument forward and holding on to the lining members, the instrument is inserted into the tube-like covering which will thereby be unfolded for precisely a required length.

According to another feature of the invention, clamp-like mounts are provided in the interior of the tube-like covering in order to hold cables and hoses projecting through the tube-like covering These mounts are preferably composed of a thermoplastic synthetic material and are riveted together by pushing their ends through recesses and then using heat to deform the ends pushed through the recesses According to a further feature of the invention, the instrument is prevented from becoming caught during insertion in an insertion direction into the tube-like covering because the folds of the tube-like covering in its telescoped configuration are arranged in such a manner that, when seen in an insertion direction of the instrument, all of the folded edges are on the exterior of the portion of the thin, flexible tube adjacent the opening region of the telescoped tube-like covering and such that the folds are oriented toward the direction of an exit opening of the tube-like covering so that catching of the surgical instrument, as could occur if the folds were oriented opposite to the introduction direction is reliably prevented. In this way, in spite of the variable extended length of the tube-like covering, it is impossible for the tip of the instrument to be inserted, which may be for example the hollow needle of an arthroscope, to get caught in lateral folds of the tube.

According to another advantageous feature, a method is provided according to which the tube-like covering can be folded into the telescoped configuration described above According to this method, the flexible tube is drawn tightly onto a mandrel, whereupon an exit opening existing at an end of the thin, flexible tube distal from the insertion opening is folded over coaxially outwardly such that it is disposed below the insertion opening. A first free opening is thereby formed by the folded edge or portion which itself is then disposed at the furthest part of the thin, flexible tube. This first free opening distal from the insertion opening is o then also "turned over" and drawn to a location several centimeters below the insertion opening. This step creates a second free opening. This second free opening as well as several later-formed free openings are "turned over" in a similar manner so that the length of the thin, flexible tube is approximately cut in half each time. In this way, the length of the thin, flexible tube can be shortened to a desired length. Due to the provision of the mandrel, "turning over" of the free opening is a simple and time-saving process. To ensure that the exit opening is disposed opposite the insertion opening and to ensure that the folded thin, flexible tube can be extended again, the exit opening is subsequently "turned over" the other folded portions, and the thin, flexible tube is then pulled off the mandrel.

After use of the method of folding of the thin, flexible tube according to the invention, the exit opening can also be partially welded shut to produce appropriate stops for a surgical instrument to be inserted or it may be provided with adhesive strips for fastening purposes.

The invention will be described in greater detail below with reference to an embodiment that is illustrated in the drawings.

BRIEF DESCRIPTION OF THE DRAWINGS

FIG. 1b is a schematic side elevational view of the thin covering of FIG. 1a.

DETAILED DESCRIPTION OF THE PREFERRED EMBODIMENT

Figure 1A:
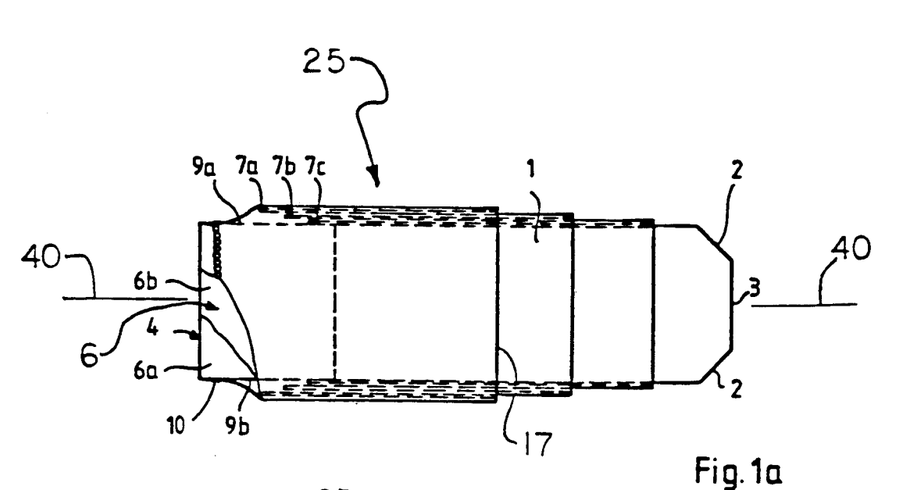
FIG. 1a is a schematic top elevational view of a thin covering for surgical instruments, the covering being in a collapsed form having folds.
Figure 1B:
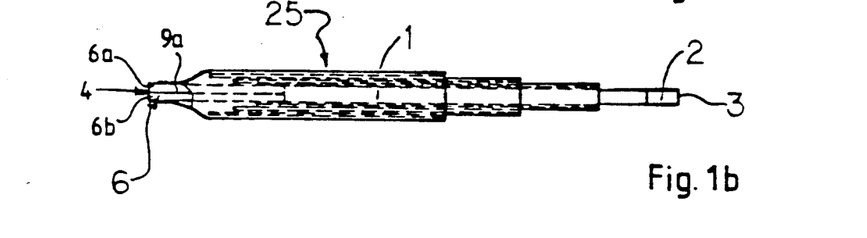

A tube-like covering 25 has a thin, flexible tube 1 which is disposed in a telescoped configuration as shown in FIGS. 1a and 1b. The thin, flexible tube 1 has a small opening 3, two lining members 6a and 6b at an insertion opening region 4, fold edges 7a, 7b and 7c, and an exit opening 17. The two lining members 6a and 6b have common opposite edge regions 9a and 9b. A weld seam 10 exists where the lining members 6a and 6b are connected to the thin, flexible tube 1. The thin, flexible tube I is telescoped longitudinally in sections along a longitudinal axis 40 so that the overall length of the tube-like covering 25 is significantly shortened. The folding is indicated schematically in FIGS. 1a and 1b and is greatly enlarged for the sake of clarity at the upper and lower edges of the tube-like covering 25 in these Figs.

Figures 2, 3A, 3B, 4:
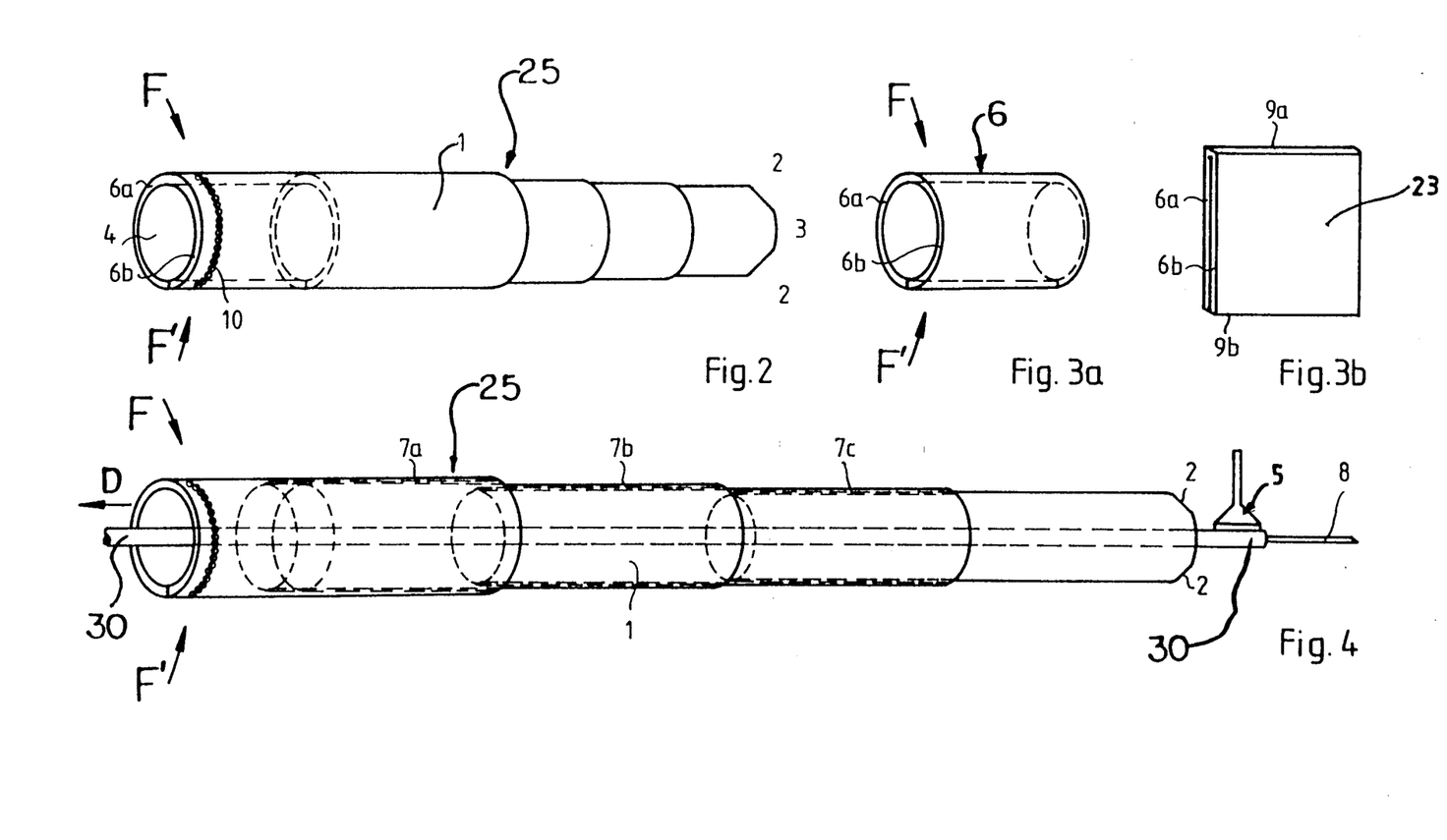
FIG. 2 is a schematic perspective view of the thin covering of FIG. 1a with a spread-open insertion opening.
FIG. 3a is a schematic perspective view of a spread-open lining for the insertion opening of FIG. 2.
FIG. 3b is a perspective view of the lining of FIG. 3a in an initial configuration corresponding to the initial lining configuration shown in FIGS. 1a and 1b.
FIG. 4 is a schematic perspective view of the thin covering of FIG. 1a during a process of pulling the thin covering over a surgical instrument.

An orthoscope 5 having a hollow needle 8 and an elongated portion 30 is shown in FIG. 4 which can easily be pushed through the tube-like covering 25 in its telescoped configuration which is shown in FIGS. 1a and 1b. To fix the orthoscope 5 at a desired insertion depth in the thin, flexible tube 1, stops 2 in the form of sealed, tapering edges are provided adjacent the small opening 3. The orthoscope 5 can be inserted through the small opening 3 at the end of the tube-like covering 25 opposite the insertion opening region 4 until the elongated portion 30, supplying the external connections of the orthoscope 5 for suction and rinsing channels, has also been inserted in thin, flexible tube 1.

To facilitate the above-mentioned insertion process, the insertion opening region 4 is equipped in its interior with two like resiliently deformable lining members 6a and 6b which are connected together at their ends to form a jaw 6 which is openable. The lining members 6a and 6b initially lie flat against each other, as shown in FIGS. 1a, 1b and 3b. The lining members 6a and 6b project into the insertion opening region 4 to such an extent that they project beyond the fold edges 7a, 7b and 7c of the initial folds of the thin, flexible tube 1. In this way, the hollow needle 8 of the orthoscope 5 is prevented from being caught in a lateral fold when it is inserted into the thin, flexible tube 1. The orthoscope 5 is introduced in the insertion opening region 4 which is spread open in the manner of a jaw 6 by slight pressure exerted in the directions indicated in FIG. 2 by arrows F, F', respectively, on the opposite edge regions 9a and 9b of the insertion opening region 4 which is equipped with lining members 6a and 6b. The insertion opening region 4 formed by the above-mentioned spreading process is shown in FIGS. 2, 3a, and 4, in which the directions of the applied forces on the opposite edge regions 9a and 9b are respectively indicated by the arrows F and F'.

The lining members 6a and 6b are preferably made of cardboard. As can be in FIGS. 3a and 3b, single rectangular piece of cardboard 23, folded at the edge region 9a, is sufficient for this purpose. As shown in FIG. 3b, the piece of cardboard 23 is folded in the middle so that two connected, identically sized superposed lining members 6a and 6b are produced. The folded piece of cardboard 23 can be fastened quickly and easily at the insertion opening region 4 of the thin, flexible tube 1 by means of the weld seam 10.

Figure 5:
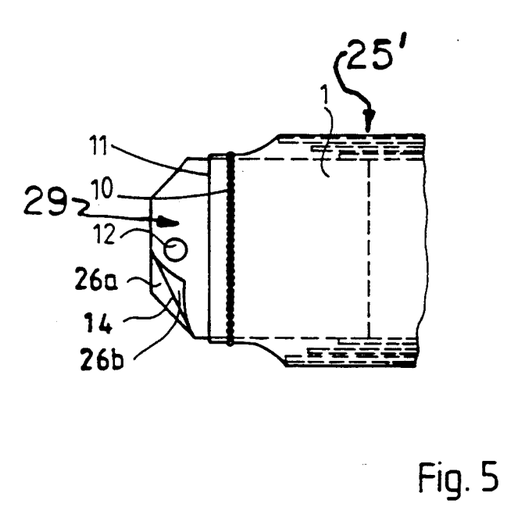
FIG. 5 is a schematic top elevational view of an opening region of a thin covering similar to that of FIG. 1, equipped with a lining which includes a gripping tab.

FIG. 5 is a plan view of an embodiment of a tube-like covering 25' having a thin, flexible tube 1' similar to that of FIGS. 1a and 1b, an insertion opening region 14 similar to the insertion opening region 4 of FIGS. 1a and 1b, and including a thin covering edge 11 formed by material from the which fastens the thin, flexible tube 1 to a pair of lining members 26a and 26b which are similar to the lining members 6a and 6b of FIGS. 1a and 1b. The lining members 26a and 26b project beyond the thin covering edge 11 and each includes a gripping hole 12, the lining members 26a and 26b forming a tab 29. The gripping tab 29 having the holes 12 can be used to facilitate the unfolding of the thin, flexible tube 1'. Moreover, in this embodiment a non-sterile region of the tube-like covering 25 can be limited to the tab 29 and its gripping hole 12 projecting beyond the covering edge 11 of the thin, flexible tube 1.

Figure 6:
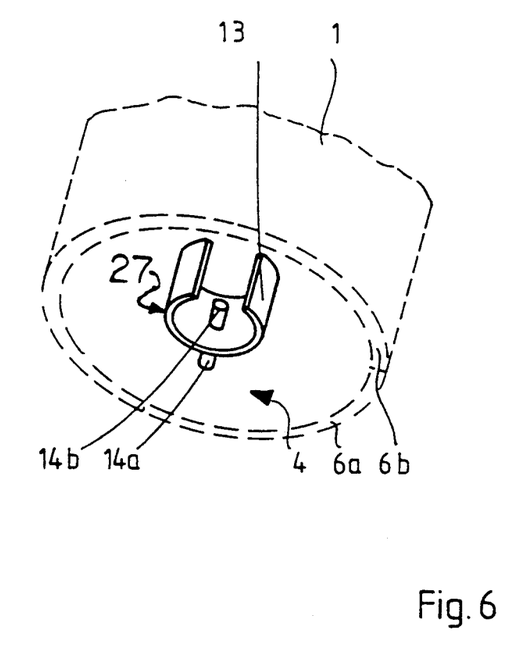
FIG. 6 is a perspective view of a cable mount within a lining member which is in an open position.

FIG. 6 shows a mount 27 for a cable or supply hose (not shown) disposed within the insertion opening region 4 (shown in dashed lines). The mount 27 is composed of an elastically spreadable cable or hose clamp 13 and two fastening rivets 14a and 14b which fasten the clamp 13 to the thin, flexible tube 1 at the insertion opening region 4, for example by hot-riveting the thermoplastic material forming the rivets 14a and 14b to the thin, flexible tube 1 and to the clamp 13. the invention for the production of folds in the thin, flexible tube 1' resulting in the folded configuration shown for the flexible tube 1 of Figs 1a and 1b. An insertion opening region 24 of the thin, flexible tube 1' is pulled over a tubular or cylindrical mandrel 16 that is fixedly connected by screws 32 and 33 to a stationary support 15. The insertion opening region 24 is similar to the insertion opening region 14 of FIG. 5. The diameter of the mandrel 16 corresponds to the inner diameter of the thin, flexible tube 1'. While a cylindrical mandrel 16 is shown in the drawings, a mandrel having a prismatic body could also be used having, e.g., a rectangular cross sectional outline (such as a flat plate), or a polygonal cross sectional outline which can be regular or non-regular.

Figure 7A:
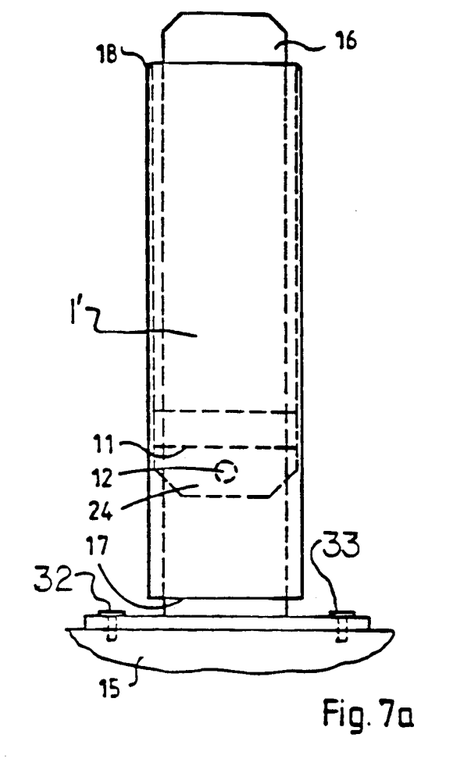
FIGS. 7a to 7d are schematic front elevational views sequentially illustrating method steps according to the invention for producing a telescoped configuration of the thin, flexible tube.

In FIG. 7a, the exit opening 17 disposed opposite the insertion opening region 24 has already been turned over—in a "flanging process"—so as to be coaxially outside of and covering the insertion opening region 24. The exit opening 17 extends below the height of the insertion opening region 24 in FIG. 7a. The thin, flexible tube 1' is folded as shown in FIG. 7a to form a first free opening 18 which is bounded by the folded portion of the thin, flexible tube 1'.

Figure 7B:
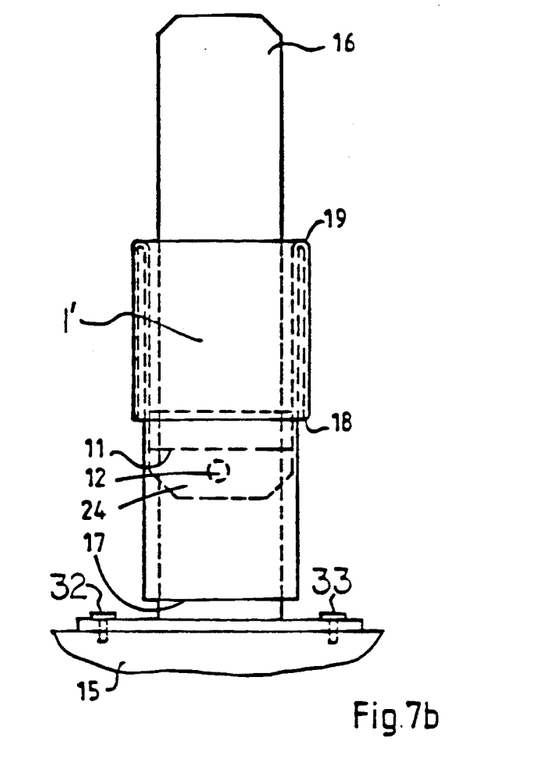
Figure 7C:
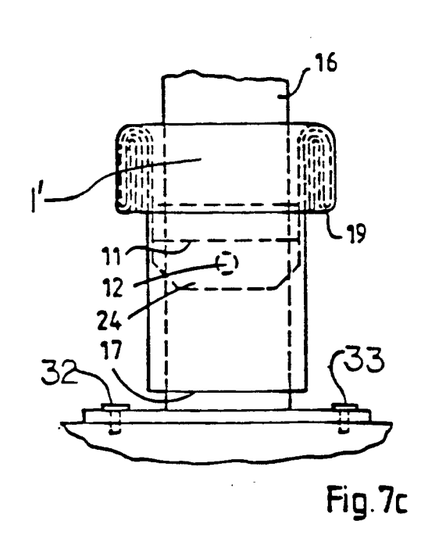

In FIG. 7b, the thin, flexible tube 1' is folded such that the first free opening 18 has been coaxially turned outwardly down to form a second free opening 19 at the uppermost portion of the thin, flexible tube 1' which is bounded by the folded portion of the thin flexible tube 1' at that location. The first free opening 19 is pulled to a location which is in the vicinity of the insertion opening region 24. As shown in FIG. 7c, the folding process is repeated once more to coaxially turn down the second free opening 19 to form a third free opening 20 created by the "flanging process".

Figure 7D:
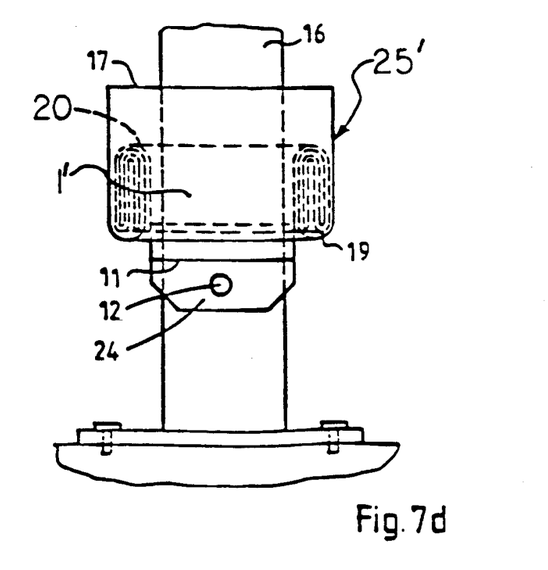

Then the projecting exit opening 17 is turned coaxially outwardly once more in an upward direction as shown in FIG. 7d so that it covers the second free opening 19 and the third free opening 20, thereby projecting above all of the folded regions of the thin, flexible tube 1'. The thin, flexible tube 1' folded as shown in FIG. 7d is then pulled upwardly off the mandrel 16. The exit opening 17 may then be partially Welded shut or provided with adhesive strips (not shown).

By the method of FIGS. 7a to 7d, the folded thin, flexible tube 1' is made to form a tube-like covering 25' by folding of the thin, flexible tube 1 into a folded configuration similar to that shown for the thin, flexible tube 1 in FIGS. 1a and 1b. In the folded configuration, the tube-like covering 25 is ready for use in which the insertion opening region 24 can be gripped so as to spread it open to permit introduction of an orthoscope 5 as shown in FIG. 4. The exit opening 17 can also be used in order for connection to the end of the orthoscope 5 or other instrument to facilitate unfolding of the tube-like covering 25 when the orthoscope 5 is advanced further.

The method steps described above with reference to FIGS. 7a to 7d employ the fact that the interior of the thin, flexible tube 1' adheres to the cylindrical mandrel 16 and can easily be pulled off at any turned-up end once the step of turning up has been accomplished by the "flanging process" described above, and in which the overlapping regions of the tube-like covering 25' can relatively easily slide against one another.

Figure 8A:
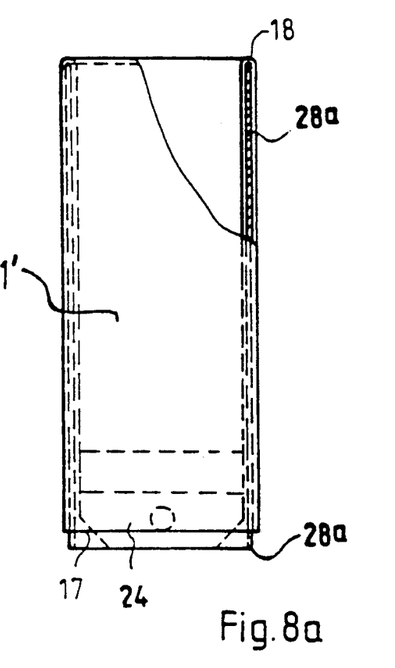
FIGS. 8a to 8c are schematic front elevational views sequentially illustrating method steps in a further embodiment of the invention for producing the telescoped configuration of the thin, flexible tube.
Figure 8B:
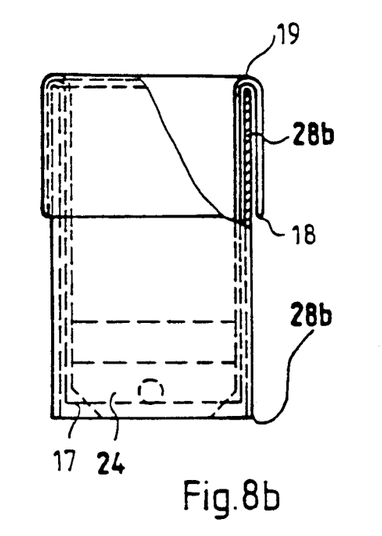
Figure 8C:
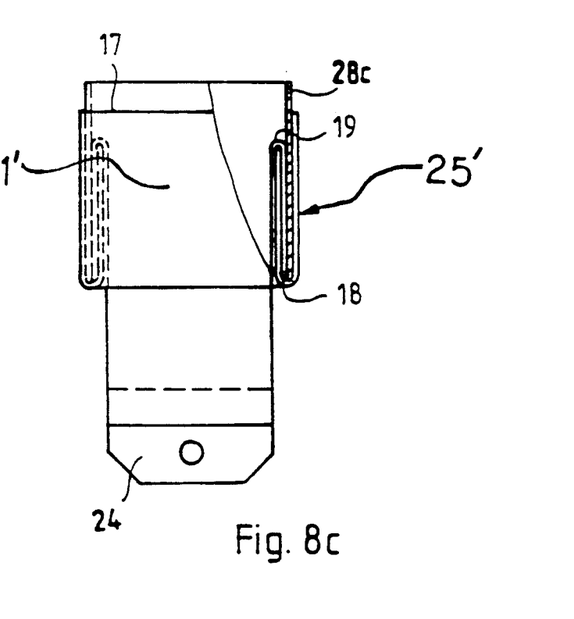

FIGS. 8a to 8c are schematic representations of steps according to a further method according to the invention for the production of the telescoping folds, with like elements in the previous Figs. having like numerals. In FIGS. 8a to 8c, instead of the mandrel 16 of the previous embodiment shown in FIGS. 7a to 7d, first, second and third thin-walled tubes 28a, 28b, and 28c are employed. The end of a thin, flexible tube 1' having an insertion opening region 24 is initially pushed as shown in FIG. 8a into the first thin-walled tube 28a. The length of the tube 28a approximately corresponds to one-half the length of the thin, flexible tube 1' so that one end of the latter including the exit opening 17 projects about the outside of the thin-walled tube 28a to a location just above the lowermost edge of the tube 28a. Then the second thin-walled tube 28b, which is shorter than the first thin-walled tube 28a, is pushed over the turned-over portion of the thin, flexible tube 1' overlying the first thin-walled tube 28a such that the bottom of the second thin-walled tube 28b is approximately level with the bottom of the first thin-walled tube 28a while the top of the first thin-walled tube 28a extends higher than the second thin-walled tube 28b. In order to be able to turn the bend forming the first free opening 18 coaxially outwardly over the second thin-walled tube 28b, the relatively long first thin-walled tube 28a is removed by pulling it out. This turning process is repeated several times with sequentially shorter tubes 28b and 28c. The last thin-walled tube 28c is pushed on only until its lower edge is disposed above the exit opening 17. The second thin-walled tube 28b tube associated with the preceding method step is removed and the exit opening 17 can then be coaxially turned upward toward the outside so that it is oriented in the direction opposite to that of the insertion to the insertion opening region 24. The tube-like covering 25' in its folded configuration is obtained by removal of the third thin-walled tube 28c from the thin, flexible tube 1', and the tube-like covering 25' is then available for further processing.

The above-described method produces a series of folds which—due to the sequential turning over of the end of the (multi-layer) thin, flexible tube 1' toward the outside—does not have any folded edges on the interior of the still folded tube-like covering 25' which would interfere with the insertion of the surgical instrument. The inner walls of the folded tube-like covering 25' have no obstacles whatsoever to impede insertion of the surgical instrument in an insertion direction D' as shown in FIG. 4.

In the foregoing description, three tubular elements 28a, 28b, and 28c are shown. Additional tubular elements can be provided, each sequential one having a larger inner diameter than the preceding one, so that additional folds can be made as shown in the step shown in FIG. 8b, wherein the newest free opening disposed at the top of FIG. 8b is folded over coaxially about the newest applied one of the tubular elements 28a, 28b, 28c, ..., until the desired number of folds is reached. Furthermore, while tubular elements 28a, instead, each having an open cross sectional outline, e.g. C-shaped elements can be used.

It will be understood that the above description of the present invention is susceptible to various modifications, changes and adaptations, and the same are intended to be comprehended within the meaning and range of the equivalents of the appended claims.

What is claimed is:

1. A thin covering for protecting an elongated surgical instrument comprising:

an elongated tube of a thin flexible sterilizable material having an insertion opening and an exit opening at opposite ends thereof;

two resiliently deformable leaf-like lining members connected to said elongated tube and disposed in said tube at said insertion opening, said lining members each having a central portion and a pair of opposite side edges, a first one of said pair of side edges of one of said lining members being substantially congruent to a first one of said pair of side edges of the other of said lining members, and a second one of said pair of side edges of said one of said lining members being substantially congruent to a second one of said pair of side edges of said other of said lining members, and wherein upon application of force to said opposite side edges urging said opposite side edges towards each other, said central portions are spread apart to cause the insertion opening to open in a jaw-like manner for receiving a surgical instrument.

2. A thin covering as defined in claim 1, wherein said resiliently deformable lining members are composed of cardboard material which is sufficiently thin that manual pressure causes the spreading apart of said central portions of said lining members to cause the insertion opening to open in a jaw-like manner, and which is sufficiently thick that said lining members resiliently return to their original shapes upon release of said manual pressure.

3. A thin covering as defined in claim 1, wherein said elongated tube is in a telescopically folded configuration and has an outside layer and an inside layer, said inside layer includes said insertion opening and said outside layer includes said exit opening.

4. A thin covering as defined in claim 1, wherein said lining members each have a substantially rectangular shape.

5. A thin covering as defined in claim 1, wherein said lining members project longitudinally beyond an edge of said elongated tube and each said lining member includes a gripping hole.

6. A thin covering as defined in claim 1, wherein said lining members are glued to said elongated tube at an interior portion of said tube at said insertion opening.

7. A thin covering as defined in claim 1, wherein said lining members are contiguously joined along their first side edges such that said lining members are in the form of a generally rectangular planar member folded along its center, at least one edge of the folded generally rectangular planar member contacting an inner surface of said tube at said insertion opening, and wherein the width of each of said lining members between opposite side edges is substantially equal to one-half of the circumferential length of said elongated tube at the insertion opening thereof.

8. A thin covering as defined in claim 1, wherein said tubular body has a longitudinal axis, and wherein said lining members have a preferential curvature which is convex on outwardly-facing surfaces, said lining members having longitudinal axes which extend in a direction generally parallel to said longitudinal axis of said tubular body.

9. A thin covering as defined claim 1, further comprising at least one clamp-like cable mount connected to said tubular body and which includes an elastically deformable U-shaped clamping region and means for connecting said clamp-like mount with the interior of said tube at said insertion opening.

10. A thin covering as defined in claim 1, wherein said lining members are composed of plastic sheet material.

11. A thin covering as defined in claim 1, wherein said lining members are composed of metal foil material.

12. A thin covering as defined in claim 1, wherein said lining members are welded to the interior of said elongated tube at said insertion opening.

* * * * *